(12) United States Patent
Roe et al.

(10) Patent No.: US 12,005,249 B2
(45) Date of Patent: Jun. 11, 2024

(54) METHOD FOR REGULATING TETS POWER TRANSFER

(71) Applicant: Medtronic, Inc., Minneapolis, MN (US)

(72) Inventors: Jacob A. Roe, North St Paul, MN (US); Joel B. Artmann, Elk River, MN (US); Jonathan P. Roberts, Coon Rapids, MN (US); David J. Peichel, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 693 days.

(21) Appl. No.: 17/174,717

(22) Filed: Feb. 12, 2021

(65) Prior Publication Data

US 2022/0257923 A1 Aug. 18, 2022

(51) Int. Cl.
```
H01M 10/44      (2006.01)
A61M 60/178     (2021.01)
A61M 60/873     (2021.01)
H01M 10/46      (2006.01)
H02J 50/12      (2016.01)
```
(52) U.S. Cl.
CPC ........ *A61M 60/873* (2021.01); *A61M 60/178* (2021.01); *H02J 50/12* (2016.02); *A61M 2205/33* (2013.01); *A61M 2205/52* (2013.01)

(58) Field of Classification Search
CPC ........ H02J 7/02; H02J 50/12; A61M 2205/33; A61M 2205/52; A61M 60/873; A61M 60/178
USPC ................................ 320/107, 139, 141, 108
See application file for complete search history.

(56) References Cited

U.S. PATENT DOCUMENTS

| 9,002,468 | B2* | 4/2015 | Shea ................... A61M 60/873 607/61 |
| 9,199,516 | B2 | 12/2015 | Jansen |
| 9,660,702 | B2* | 5/2017 | Madawala .............. B60L 55/00 |
| 10,193,375 | B2 | 1/2019 | Tustin et al. |
| 10,226,636 | B2* | 3/2019 | Gaddam .............. A61N 1/3787 |
| 2013/0158631 | A1 | 6/2013 | Shea et al. |
| 2014/0203659 | A1 | 7/2014 | Madawala et al. |

(Continued)

FOREIGN PATENT DOCUMENTS

| DE | 112012002922 T5 | 3/2014 |
| EP | 2232668 A1 | 9/2010 |
| EP | 2985879 A1 | 2/2016 |

(Continued)

OTHER PUBLICATIONS

International Search Report and Written Opinion of International Application No. PCT/US2022/014818, dated May 12, 2022, 7 pp.

*Primary Examiner* — Edward Tso
(74) *Attorney, Agent, or Firm* — Shumaker & Sieffert, P.A.

(57) ABSTRACT

In an implanted medical device system, an internal controller, external power transmitter and methods for regulation of TETS power for an implanted medical device system are disclosed. According to one aspect, a method in an external power transmitter of an implanted medical device system includes determining a current in an external coil of the external power transmitter, multiplying the determined current by a supply voltage to determine a power delivered to the external coil, and controlling the power delivered to the external coil by adjusting the current in the external coil.

17 Claims, 5 Drawing Sheets

(56) References Cited

U.S. PATENT DOCUMENTS

2018/0043167 A1    2/2018  Gaddam et al.

FOREIGN PATENT DOCUMENTS

| KR | 20110074750 A | 7/2011 |
|---|---|---|
| WO | 2010030378 A1 | 3/2010 |

* cited by examiner

FIG. 1

Prior Art

METHOD FOR REGULATING TETS POWER TRANSFER

CROSS-REFERENCE TO RELATED APPLICATION n/a

FIELD

The present technology is generally related to implantable medical devices such as a left ventricular assist device (LVAD), and more particularly to regulation of TETS power for an implanted medical device system.

BACKGROUND

Figure 1:
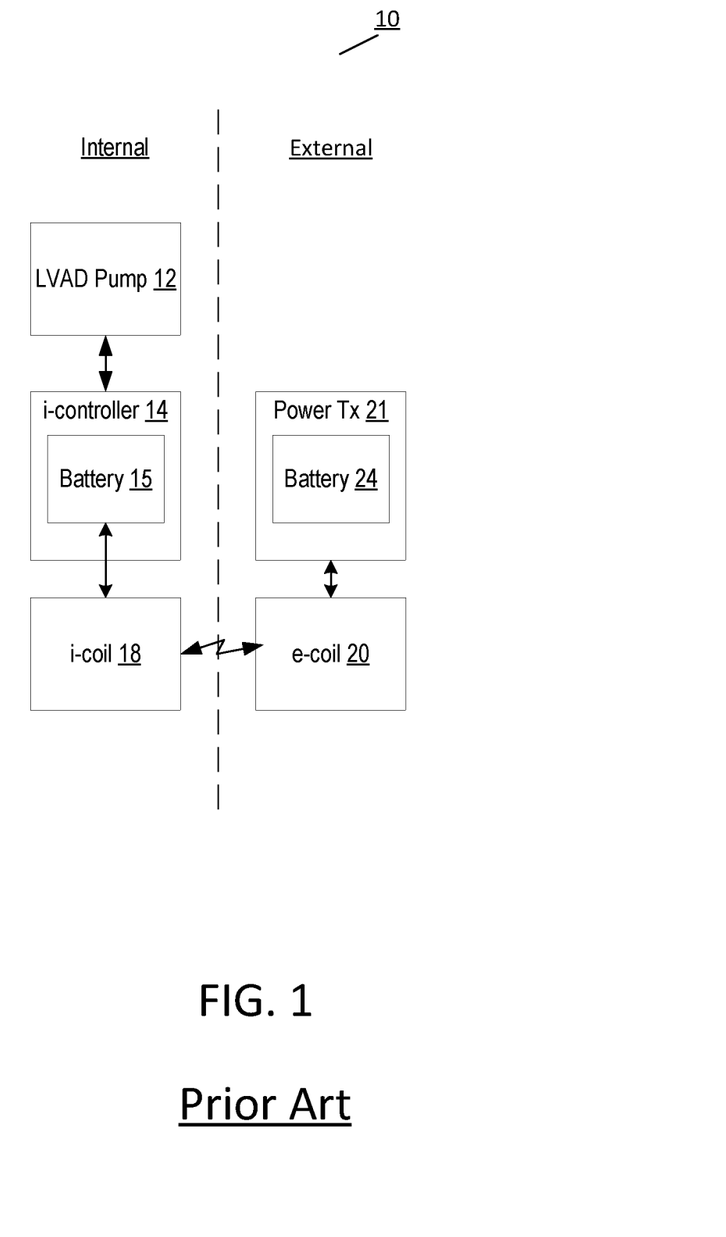
FIG. 1 is a block diagram of an implantable LVAD system.

Referring to FIG. 1, an implantable LVAD system 10 has internal components (in the body of the patient) and external components. The LVAD system 10 may typically include an LVAD pump 12, an implanted controller (i-controller) 14 having an internal battery 15, an implanted internal transcutaneous energy transfer system (TETS) coil (i-coil) 18, an external TETS coil (e-coil) 20 and an external power transmitter 21 with a detachable battery 24. In operation, power is supplied from the external power transmitter 21 to the i-controller 14 via mutual coupling of the coils 18 and 20, in order to charge the internal battery 15 of the i-controller 14 and to power the LVAD pump 12. The coils 18 and 20 transfer power via electromagnetic energy over the air and through the body. The power supplied by the external power transmitter 21 may come from the detachable battery 24 or from a wall outlet, for example.

SUMMARY

The techniques of this disclosure generally relate to regulation of TETS power for an implanted medical device system.

The present disclosure provides an implanted medical device system, such as a left ventricular assist device (LVAD) system. The implanted medical device system includes at least an internal controller, an internal implanted device controlled by the internal controller and an external power transmitter in communication with the internal controller.

According to one aspect, an external power transmitter of an implanted medical device system is provided. The external power transmitter includes processing circuitry configured to determine a current in an external coil of the external power transmitter, multiply the determined current by a supply voltage to determine a power delivered to the external coil, and control the power delivered to the external coil by adjusting the current in the external coil.

According to this aspect, in some embodiments, the power is controlled by adjusting a duty cycle of a pulse-width-modulated bridge circuit. In some embodiments, the current is determined while the bridge circuit is active. In some embodiments, the current in the external coil is estimated based at least in part on peak coil current, a pulse width of the bridge circuit, and an assumption that the current is approximated by a sine wave. In some embodiments, the processing circuitry is further configured to adjust the power to account for resistive losses in the external coil. In some embodiments, the supply voltage is used to compensate a current proportional integral derivative (PID) controller to maintain a constant power over different supply voltages. In some embodiments, the current is determined by continuous measurement of a bridge circuit output. In some embodiments, determining the current includes measuring a peak current in the external coil.

According to another aspect, a method in an external power transmitter of an implanted medical device system is provided. The method includes determining a current in an external coil of the external power transmitter, multiplying the determined current by a supply voltage to determine a power delivered to the external coil, and controlling the power delivered to the external coil by adjusting the current in the external coil. In some embodiments, the power is controlled by adjusting a duty cycle of a pulse-width-modulated bridge circuit. In some embodiments, the current is determined while the bridge circuit is active. In some embodiments, the current in the external coil is estimated based at least in part on peak coil current, a pulse width of the bridge circuit, and an assumption that the current is approximated by a sine wave. In some embodiments, the method further includes adjusting the power to account for resistive losses in the external coil. In some embodiments, the supply voltage is used to compensate a current proportional integral derivative (PID) controller to maintain a constant power over different supply voltages. In some embodiments, the current is determined by continuous measurement of a bridge circuit output. In some embodiments, determining the current includes measuring a peak current in the external coil.

According to yet another aspect, a current control loop in an external device of an implanted medical device system is provided. The current control loop includes an H-bridge circuit configured to output a current to an external coil of the external device, and processing circuitry. The processing circuitry is configured to determine a current to the external coil based on the current output of the H-bridge circuit, multiply the determined current by a supply voltage applied to the external coil to determine a power delivered to the external coil, and control the power delivered to the external coil by adjusting the current in the external coil, the adjusting being by controlling a pulse width modulation (PWM) duty cycle of the H-bridge circuit in response to the determined current.

According to this aspect, in some embodiments, the current control loop also includes a current proportional integral derivative (PID) controller configured to control the PWM duty cycle of the H-bridge circuit. In some embodiments, the current control loop further includes a current sensor configured to measure the current of the external coil, the processing circuitry being configured to compare the measured current to a current that is based on a difference between a voltage across an internal coil of the implanted medical device system and a target voltage. In some embodiments, the H-bridge output current is based on a supply voltage provided by a power supply external to the external device.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Some embodiments described herein are related to regulation of TETS power for an implanted medical device system. In a TETS with resonant inductive-capacitive circuits for transmission and reception, alternating current (AC) power is introduced to a system for transfer using an H-bridge drive configuration from a DC power source. Control of the duty cycle or pulse width of the H-bridge drive is one method to control the power level delivered to the implanted circuitry of the implanted medical device system. However, the output power available and the current levels in the i-coil 18 and e-coil 20 are not directly controllable by control of the duty cycle or pulse with of the H-bridge drive. Measuring the peak or root-mean-squared (RMS) current level in the e-coil 20 and adjusting the duty cycle to maintain constant current can constrain the current level in the e-coil 20, but may still allow delivery of an available power level that varies in response to changing operating conditions.

Thus, some embodiments provide for measuring and controlling the power delivered from the power supply to the primary coil to maintain nearly constant power available from the secondary coil. Further refinement of the controlled power level accounts for resistive losses in the primary coil. Measurement of the power delivered to the primary coil can be performed by measuring the current input to the primary coil while the H-bridge is active and multiplying the measured current by the DC voltage to obtain a measure of power. The current measurement can be a continuous measurement on the H-bridge drive. Alternatively, the current measurement can be an estimate based on RMS or peak primary coil current and knowledge of the H-bridge pulse width, further combined with knowledge that the current can be closely approximated by a sine wave.

Figure 2:
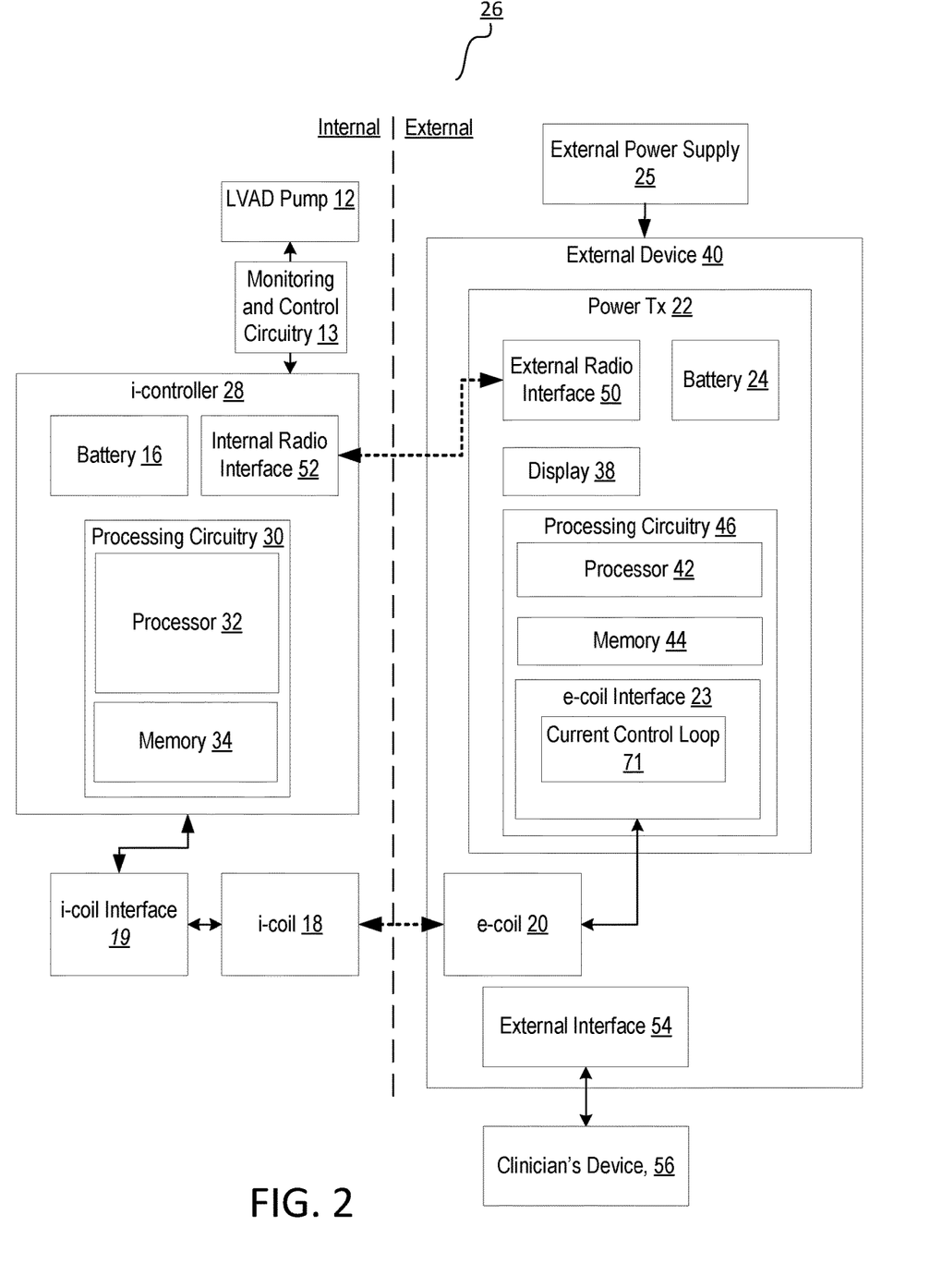
FIG. 2 is a block diagram of an embodiment of an implanted medical device system that implements a process of regulation of TETS power for an implanted medical device system.

FIG. 2 shows a block diagram of one example configuration of an implanted medical device system 26 having external components such as an external power transmitter 22, and internal components such as an internal controller (i-controller) 28 configured to perform functions described herein. As used herein, the term "implanted medical device system 26" refers to the system that includes both the implanted/implantable components as well as external components described herein.

The i-controller 28 may have processing circuitry 30 which may include a processor 32 and an internal memory 34. The processor 32 may be configured to execute computer instructions stored in the internal memory 34. Those instructions may include instructions to cause the processor to perform some of the processes described in more detail below.

A message or result from the i-controller 28 may be transferred from the i-controller 28 to an external display 38 of an external device 40, which may include a processor 42 and a memory 44 within processing circuitry 46, the external power transmitter 22 and the detachable battery 24, as well as the e-coil 20 in some embodiments. The memory 44 may be configured to store computer instructions to be executed by the processor 42. The external display 38 may be configured to display information received from the i-controller 28. In some embodiments, an external power supply 25 may provide power to the external power transmitter 22.

The processing circuitry 30 and/or 46 may comprise integrated circuitry for processing and/or control, e.g., one or more processors and/or processor cores and/or FPGAs (Field Programmable Gate Array) and/or ASICs (Application Specific Integrated Circuitry) adapted to execute instructions. The processor 32, 42 may be configured to access (e.g., write to and/or read from) the memory 34, 44, respectively, which may comprise any kind of volatile and/or nonvolatile memory, e.g., cache and/or buffer memory and/or RAM (Random Access Memory) and/or ROM (Read-Only Memory) and/or optical memory and/or EPROM (Erasable Programmable Read-Only Memory).

The processing circuitry 30 and/or 46 may be configured to control any of the methods and/or processes described herein and/or to cause such methods, and/or processes to be performed. Processors 32, 42 each comprise multiple processors. The memory 34, 44 is configured to store data, programmatic software code and/or other information described herein. In some embodiments, the software stored in the memory 34, 44, may include instructions that, when executed by the processor 32, 43, respectively, and/or processing circuitry 30, 46, respectively, causes the processor 32, 43 and/or processing circuitry 30, 46 to perform the processes described herein with respect to the i-controller 28 and the external power transmitter 22.

Electrical communication of signals and power between the internal components of i-controller 28 may be via communication busses and individual electrical conductors not shown in FIG. 2. For example, a multi-conductor address bus and data bus may connect processor 32 with internal memory 34. In some embodiments, an i-coil interface 19 associated with i-coil 18 may be included in the set of internal components making up the implanted medical device system 26. One purpose of i-coil interface 19 may be to modulate the alternating current applied to the i-coil 18 with signals from the i-controller 28 to be transmitted from the i-coil 18 to the e-coil 20 and/or to demodulate signals to be received by the i-coil 18 from the e-coil 20. In some embodiments, a purpose of the i-coil interface 19 is to provide conversion between the alternating current (AC) of the i-coil 18 and direct current (DC) to charge the battery 16.

The power supplied to the i-coil 18 may be adjusted by varying the AC electrical current in the e-coil 20. Some or all functions of the i-coil interface 19 may be included in the i-controller 28 and/or the i-coil 18. In some embodiments, the i-coil 18 and/or i-coil interface 19 may be internal to or considered part of the internal controller 28. Similarly, electrical communication of signals and power between the internal components of external device may be by communication busses and individual electrical conductors not shown in FIG. 2. For example, a multi-conductor address bus and data bus may connect processor 42 with memory 44. In some embodiments, an e-coil interface 23 associated with e-coil 20 may be included in the set of external components making up the implanted medical device system 26. The e-coil interface 23 may include a TETS interface configured to demodulate information signals from the processing circuitry 30 transmitted from the i-coil 18 to the e-coil 20. The e-coil interface 23 may also be configured to couple power from the external power transmitter 22 to the e-coil 20. In some embodiments, the e-coil interface 23 may be two distinct units, one unit for demodulation of signals from the i-controller that are uploaded via the coils 18 and 20, and one unit for coupling power from the external power transmitter 22 to the e-coil 20. In some embodiments, the i-controller 28 may upload information to the external power transmitter 22 via the coils 18 and 20, but the power transmitter does not download information to the i-controller 28 via the coils 18 and 20. In some embodiments, the e-coil interface 23 may include all or some of the components of a current control loop 71 that is configured to control power transfer from the e-coil 20 to the i-coil 18.

In some embodiments, the internal components of the implanted medical device system 26 may include monitoring and control circuitry 13. A purpose of monitoring and control circuitry 13 may include monitoring speed and temperature, for example, of the LVAD pump 12. Another purpose of the monitoring and control circuitry 13 may include controlling the speed of the LVAD pump 12. Another purpose of the monitoring and control circuitry 13 may include monitoring the temperature of the i-controller 28, the i-coil 18 and/or the implanted battery 16. In some embodiments, some or all of the monitoring and control circuitry 13 may be incorporated into the LVAD pump 12 and/or the i-controller 28. In some embodiments, some or all of the functions performed by the monitoring and control circuitry 13 may be performed by the processing circuitry 30. Thus, in some embodiments, the monitoring and control circuitry 13 may include one or more temperature sensors embedded in the LVAD pump 12, the i-controller 28, the i-coil 18 and/or implanted battery 16. Information obtained from and/or about the LVAD pump 12, such as speed and temperature, may be sent to the external device 40 to be displayed by external display 38. Note that although an LVAD pump 12 is shown, other internal devices may be powered and controlled by the i-controller 28 instead of or in addition to an LVAD pump 12.

The various internal components making up the LVAD system may be grouped into one or more separate housings. Similarly, the various external components making up the LVAD system may be grouped into one or more separate housings. Further, some of the components shown and described as being internal to the i-controller 28 may be instead, external to i-controller 28 in some embodiments. Similarly, some of the components shown and described as being internal to the external device 40 may be instead, external to external device 40, in some embodiments. Note further that some of the functions performed by processor 32 may be performed instead by processor 42.

Note that transfer of information from the external device 40 to the internal memory 34, and vice versa, may be by wireless radio frequency (RF) transmission (over the air and through the body when the i-controller 28 is implanted). Accordingly, in some embodiments, the external device 40 includes an external radio interface 50 and the i-controller 28 includes an internal radio interface 52. In some embodiments, the external radio interface 50 and the internal radio interface 52 are RF transceivers having both an RF receiver for receiving information wirelessly and an RF transmitter for transmitting information wirelessly. Such RF transceivers may be Bluetooth and/or Wi-Fi compliant, for example. In some embodiments, the RF receiver and RF transmitter within the external device 40 or within the i-controller 28 are integrated into one unit, whereas in some embodiments, they could be physically separate units.

Also, information may be communicated to the i-controller 28 from the external power transmitter 22 via the coils 18 and 20, by modulating a parameter of power transmission, such as modulating the frequency of the transmitted power, or by modulating a parameter of the i-coil interface 19, for example, by modulating a tuning capacitance of the i-coil interface 19 or by modulating the load level of the i-controller and/or the i-coil interface 19.

The external device 40 could be a patient's external device that has an external interface 54 which provides an interface between the external device 40 and a clinician's device 56. The clinician's device might, for example, have a USB port and interface 54 might include a USB port, so that a USB cable may connect the two ports. The clinician's device 56 may read data from the external device 40 and write information and control signaling to the external device 40, in some embodiments. In the alternative to a wireline connection, the interface 54 could include or be a radio interface.

Figure 3:
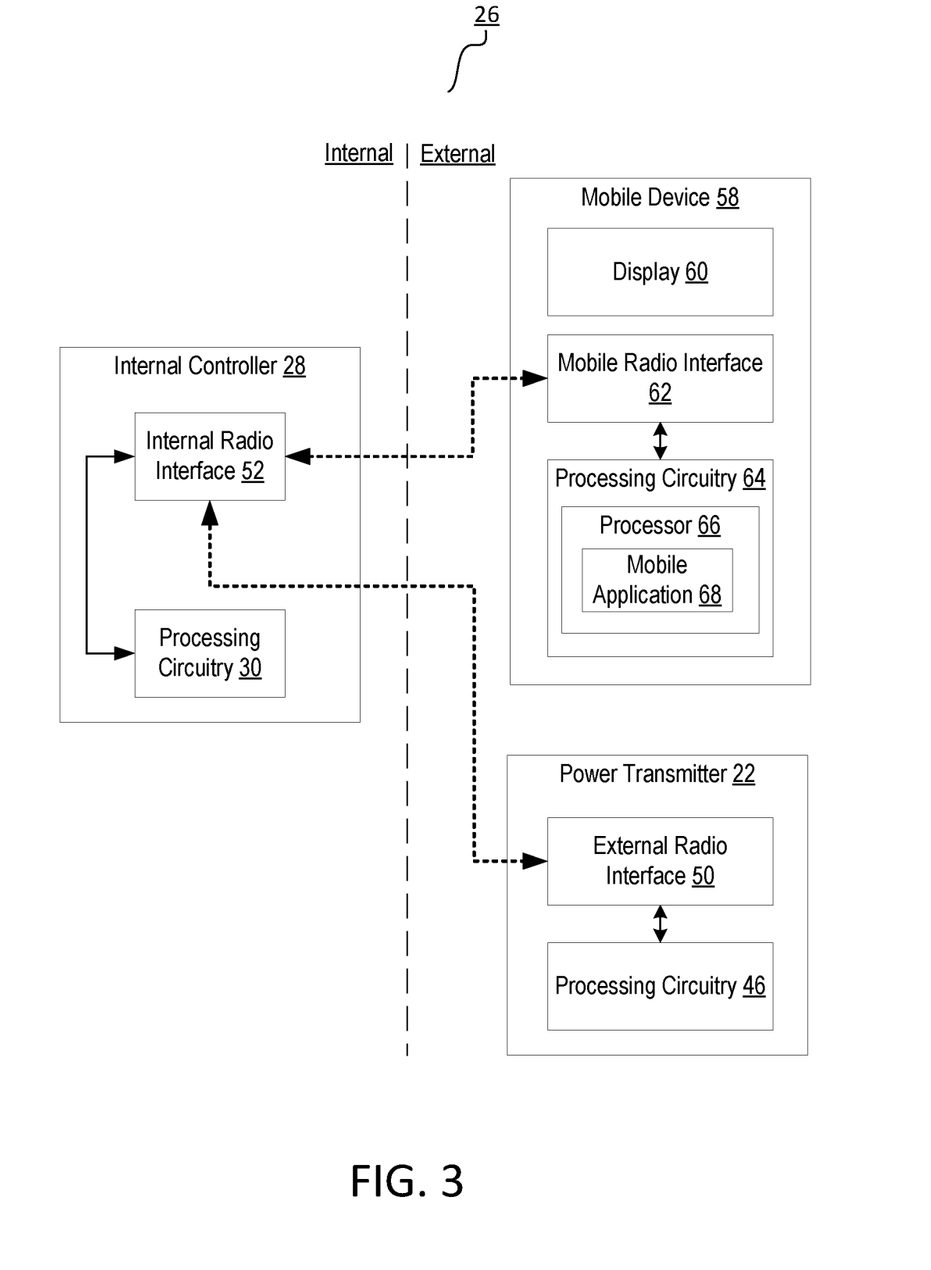
FIG. 3 is a block diagram of an implanted medical device system that includes a mobile device with a mobile application in wireless communication with an internal controller of the implanted medical device.

FIG. 3 is a block diagram of an implanted medical device system 26 that includes a mobile device 58 with a mobile application 68 in wireless communication with the i-controller 28. The mobile device 58 may be a mobile phone or other mobile digital device that can process information and communicate wirelessly with the i-controller. Accordingly, the mobile device 58 has a display 60, a mobile radio interface 62, processing circuitry 64, processor 66 which runs the mobile application 68. The radio interfaces 50, 52 and 62 may be Bluetooth Low Energy compatible radio interfaces, and the i-controller 28 may be a peripheral device responsible for advertising, while the mobile device 58 and the external power transmitter 22 may operate as master or central devices responsible for scanning and issuing connection requests.

Communication from the i-controller 28 to the external power transmitter 22 enables display on external display 38 of implanted device information such as pump data and alarm indications. The i-controller 28 may exchange, via the radio interfaces 50 and 52, diagnostic and log file data with the external power transmitter 22. The i-controller 28 may receive programming commands from an external device such as the clinician's device 56 or mobile device 58. Further, communication from the i-controller 28 to the mobile device 58, via the radio interfaces 52 and 62, enables remote monitoring in cases where the mobile device 58 is connected to the Internet, and enables the display 60 to display information about the state of the implanted portion of the implanted medical device system 26 such as, for example, remaining battery runtime. In some embodiments, the internal radio interface 52 may only communicate with the external radio interface 50 and the mobile radio interface 62 one at a time. In some embodiments, when the i-controller 28 is not engaged in a communication session with an external device, such as external power transmitter 22 or mobile device 58, the i-controller 28 may advertise continually to enable rapid reestablishment of the wireless connection between the i-controller 28 and the external power transmitter 22 or mobile device 58. Conversely, either one or both of the external power transmitter 22 or mobile device 58 may scan for such advertisements. In some embodiments, the mobile device 58 may be configured with the mobile application 68 to perform some or all of the functions attributable herein to the power transmitter 22.

Figure 4:
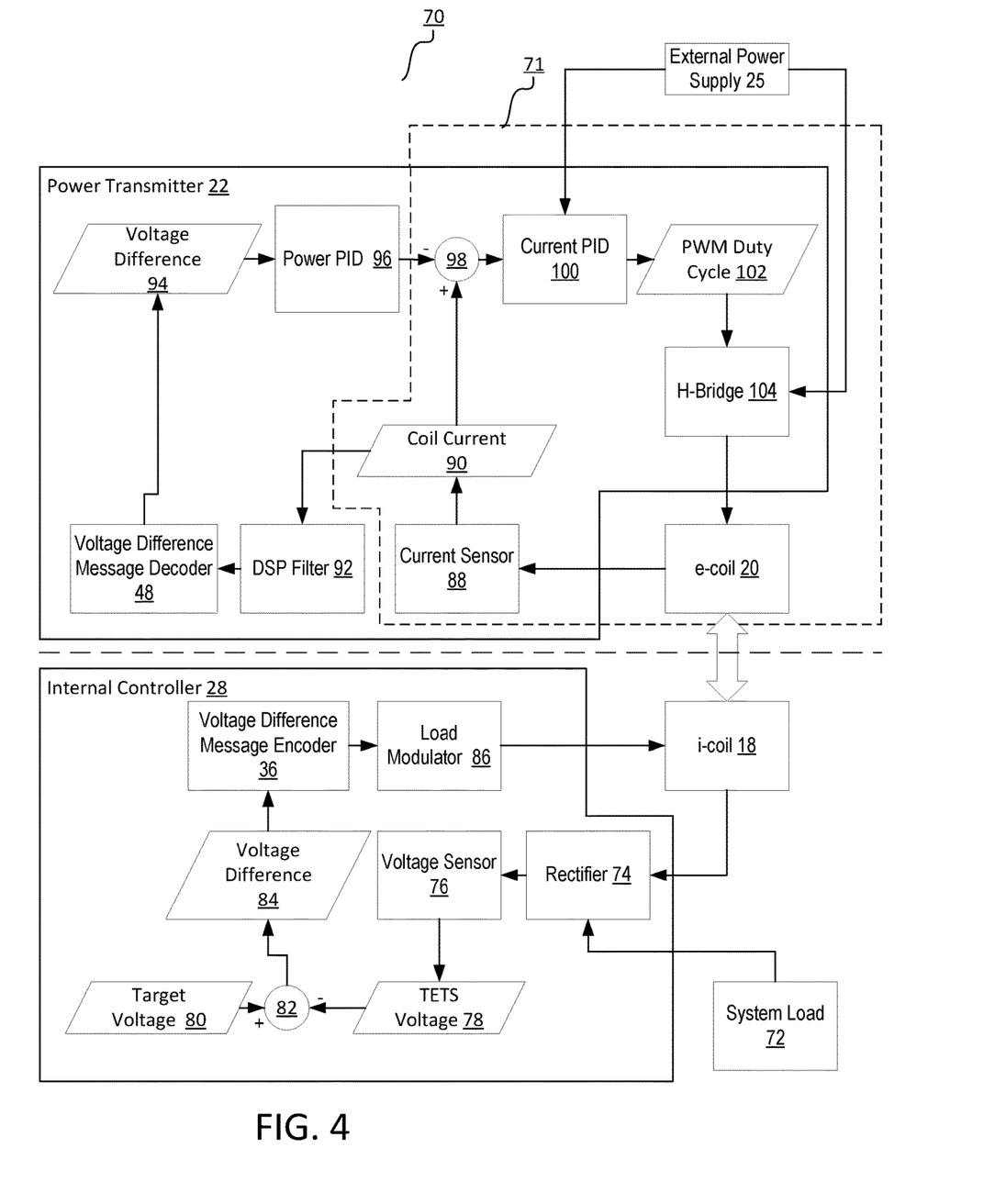
FIG. 4 is a block diagram of a coil current control loop constructed in accordance with principles set forth herein.

FIG. 4 is a block diagram of closed loop power regulation of a TETS that supplies power to an implanted medical device. The closed loop 70 includes components of the processing circuitry 30 of the i-controller 28 and components of the processing circuitry 46 of the power transmitter 22, as well as the internal coil 18 and external coil 20. The closed loop 70 includes a current control loop 71. The i-controller 28 includes the voltage difference message encoder 36 and the power transmitter 22 includes the voltage difference message decoder 48.

An object of the closed loop power regulation provided by the closed loop 70 is to apply a predetermined constant voltage to the system load 72 of the implanted medical device of the implanted medical device system 26. The system load 72 may be the load of the LVAD pump 12 or other implanted device, the load of the i-controller 28 (including the internal battery 16), and optionally also the load of the i-coil interface 19 and the monitoring and control circuitry 13. The system load 72 may be an electrical load at an input to a rectifier 74. The rectifier 74 also has an input that is electrically coupled to the i-coil 18. A purpose of the rectifier 74 is to rectify the voltage output of the i-coil 18. The rectification by the rectifier 74 may be based at least in part on the load presented by the system load 72. The rectified voltage output of the rectifier 74 is sensed by the voltage sensor 76. The voltage sensor 76 produces an output that is stored in the internal memory 34 of the i-controller 28 as the TETS voltage 78. The TETS voltage 78 is subtracted from a target voltage 80 by an adder 82 to produce the voltage difference 84. The target voltage 80 may be stored in the internal memory 34 of the i-controller 28 and may be equal to or be based on a desired voltage across the internal battery 16 of the i-controller 28. The voltage difference 84 is sent to the power transmitter 22 to be used to adjust the power transferred to the i-coil 18 in order to drive the voltage difference 84 to zero.

To send the voltage difference 84 to the power transmitter 22, the voltage difference 84 may first be encoded by the voltage difference message encoder 36 by, for example, modulating a digital form of the voltage difference 84 onto an analog signal. The encoded voltage difference message may be modulated onto the alternating current (AC) passing through the i-coil 18 by the load modulator 86. The load modulator 86 modulates the encoded voltage difference message onto the alternating current passing through the i-coil in such a way as to transmit the encoded voltage difference message to the power transmitter 22 via the mutual induction between the i-coil 18 and the e-coil 20. For example, the encoding and/or modulating by the voltage difference message encoder 36 and the load modulator 86 may include on off keying (OOK) and/or binary phase shift keying (BPSK) to encode and/or modulate the voltage difference message. Other modulation schemes may be employed such as multilevel amplitude shift keying (ASK) or higher order phase shift keying such as quadrature phase shift keying (QPSK). For example, in some embodiments, OOK may be used to signal the encoded voltage difference 84 and BPSK may be used to signal secondary performance information such as charging rate of the internal battery 16, power consumption by the LVAD pump 12, temperature of the internal electronics and/or the LVAD pump 12, as well as status of any of one or more processes implemented by the internal controller 28.

Thus, power is transferred from the power transmitter 22 to the internal controller 28 via the coils 18, 20 and, possibly simultaneously, the encoded voltage difference message is transferred from the internal controller 28 to the power transmitter 22 via the same two coils 18 and 22. The voltage difference message may include the voltage difference 84, as well as the secondary performance information as well as any other information to be sent with the voltage difference 84.

In the power transmitter 22, the current in the e-coil 20 is sensed by the current sensor 88 which outputs the e-coil current 90. The e-coil current 90 carries the encoded voltage difference message that was encoded by the voltage difference message encoder 36. The e-coil current 90 is filtered (and/or demodulated) by the digital signal processor (DSP) filter 92. For example, the DSP filter 92 could be a finite impulse response (FIR) filter. In some embodiments, the DSP filter 92 extracts the encoded voltage difference message that is carried by the e-coil current 90. The voltage difference message decoder 48 decodes the encoded voltage difference message to produce the decoded voltage difference 94. This may equal or approximately equal the voltage difference 84 determined as a difference between the TETS voltage 78 and the target voltage 80.

In some embodiments, there may be a delay between the time of determining a voltage difference 84 and the time of determining the corresponding decoded voltage difference 94. This delay may affect how closely the closed loop 70 maintains the TETS voltage 78 at the target voltage 80 and may affect damping of the closed loop 70.

A power proportional integral derivative (PID) controller 96, in response to the decoded voltage difference 94, generates a current adjustment signal that is subtracted from the coil current 90 by an adder 98 to produce current error signal. In response to the current error signal, a current PID controller 100 determines a pulse width modulation (PWM) duty cycle 102 to control the current in the e-coil 20 via a driver such as an H-bridge 104. A purpose of one or both of the power PID controller 96 and the current PID controller 100 may be to dampen any overshoot without excessive damping of the control loop.

An objective of the closed loop 70 is to continually drive the voltage difference 84, 94 toward zero so that the TETS voltage 78 is maintained at the target voltage 80. When the voltage difference 84, 94 is small, the current error signal input to the current PID controller 100 is small, resulting in a small change in the PWM duty cycle. When the change in the PWM duty cycle is small, the change in current driving the coil is small, which in turn results in only a small change in the TETS voltage 78. This small change in the TETS voltage 78 should result in even a smaller voltage difference 84. This causes the TETS voltage 78 to be maintained at or very close to the target voltage 80.

Note that in some embodiments, the communication between the i-controller 28 and the power transmitter 22 may be synchronized. In some embodiments, the AC signal applied to the e-coil 20 is used as the synchronization clock. This reduces complexity. A low quantity of communication pulses per data bit such as one communication pulse per data bit may be transferred over 4 to 8 cycles of the AC signal applied to the e-coil 20. This enables a fast enough update rate to drive the voltage difference to a negligible value. Note also that only the voltage difference 84 is fed back to the power transmitter, rather than the TETS voltage 78. This reduces the amount of data to be transmitted for closed loop power regulation. Note that the external power supply 25 may provide input to the current PID controller 100 and/or to the e-coil 20. In the alternative, or in addition, the battery 24 may supply input to the current PID controller 100.

In some embodiments, the current control loop 71 measures the e-coil current 90 while the H-bridge 104 is active. The e-coil current 90 may be multiplied by the voltage supplied to the e-coil 20 to obtain a measure of power. The e-coil current 90 as measured by the current sensor 88 can be a continuous measurement on the H-bridge 104 output. Alternatively, the current measurement can be based on the peak e-coil 20 current and knowledge of the H-bridge 104 pulse width combined with an assumed sinusoidal form of the coil current 90. Measuring and controlling the power delivered to the e-coil 20 may maintain a nearly constant power level available from the i-coil 18. Further, extra power may be applied to the e-coil 20 to account for resistive losses in the e-coil 18. By measuring current peaks in the e-coil 20, the pulse width modulation duty cycle of the H-bridge 104 may be adjusted to maintain a constant power delivered to the i-coil 18. The supply voltage across the e-coil 20 can be measured and used to compensate the gains of the current PID controller 100 to maintain consistent performance across multiple supply voltages.

Alternatives to regulating to achieve a constant power delivered to the e-coil 20 include regulating to achieve: constant peak voltage in the e-coil 20, constant per cycle average current delivered to the e-coil 20, and constant PWM pulse width applied by the H-bridge 104 to the e-coil 20. Advantages to regulating to achieve a constant power delivered to the e-coil 20 include lower sensitivity of the power level to changes in e-coil 20 to i-coil 18 alignment and positioning. Another advantage in some embodiments is lower probability of shunting caused by fast changes in coil-to-coil coupling. Another advantage in some embodiments is reduced sensitivity to coil motion in the presence of poor communication, which can be caused by external factors such as electromagnetic interference or by rapid coil movement that degrades communication. Alternative methods for regulating the power delivered to the e-coil 20 may include measuring a power level on a cycle-by-cycle basis by measuring the average current of the H-bridge 104 and measuring the bridge supply voltage, where the power is the product of the average current and the bridge supply voltage. Another method for regulating the power delivered to the e-coil 20 includes measuring a power level on a cycle-by-cycle basis by measuring peak coil current and bridge supply voltage. The method includes computing the product of the peak coil current and bridge supply voltage, further times the H-bridge pulse width times a sine wave correction factor.

The current control loop 71 is a fast control loop compared to the slow control loop that includes the internal controller components, the DSP filter 92, voltage difference message decoder 48 and power PID 96. The slow control loop may set the target voltage for the fast control loop 71.

As noted above, in some embodiments, the power is controlled by adjusting the duty cycle of the H-bridge 104. Let V*I be the instantaneous applied power applied to the e-coil 20. The average applied power is the average of V*I over a cycle. V is the supply voltage during the PWM "on" time, and 0 during the PWM "off" time. The supply voltage may be assumed to be constant during an individual PWM cycle, but may slowly change, as the battery 24 in the external power transmitter 22 is drained or as the external power transmitter 22 transitions from running untethered (from battery 24) to running from wall power. The supply voltage change can be compensated.

In contrast to the assumption that the supply voltage is constant over an individual PWM cycle, the current in the coil is not constant during the PWM cycle. Rather, the current is assumed to be sinusoidal, peaking at the center of the PWM drive and dropping to zero at the points of maximum PWM drive width (and inverting for the opposing phase of PWM operation). This means that V*I during application of the PWM drive will not be constant, but will have a partial sine wave shape (peaking in the middle of the PWM drive).

In some embodiments, voltage may be directly measured by digitizing the supply voltage for the drive of the H-bridge 104, as it changes slowly enough to be considered constant during individual bridge drive cycles.

The peak current in the e-coil 20 may be determined using the sine wave approximation for delivered power. The approximation includes the PWM pulse width, peak current and measured supply voltage. The measurements for this approximation will be available on each PWM drive cycle.

Another way to determine the current in the e-coil 20 involves measuring the average current input to the H-bridge 104, which when multiplied by the bridge supply voltage will provide the average applied power. In order to obtain the average supply current, there may be a low pass filter applied to the measurement of the supply current, which means that the rate of "new" measurements of power will be related to the applied lowpass filter rather than the PWM update rate. This will be slower than the rate available from the peak current measurement and calculations. but will also not be subject to use of assumptions. Further, the update rate will still be faster than the rate of data being transmitted over the communication link, retaining some benefit of faster response time to changes in the positioning and orientation of the e-coil 20 with respect to the i-coil 18.

Figure 5:
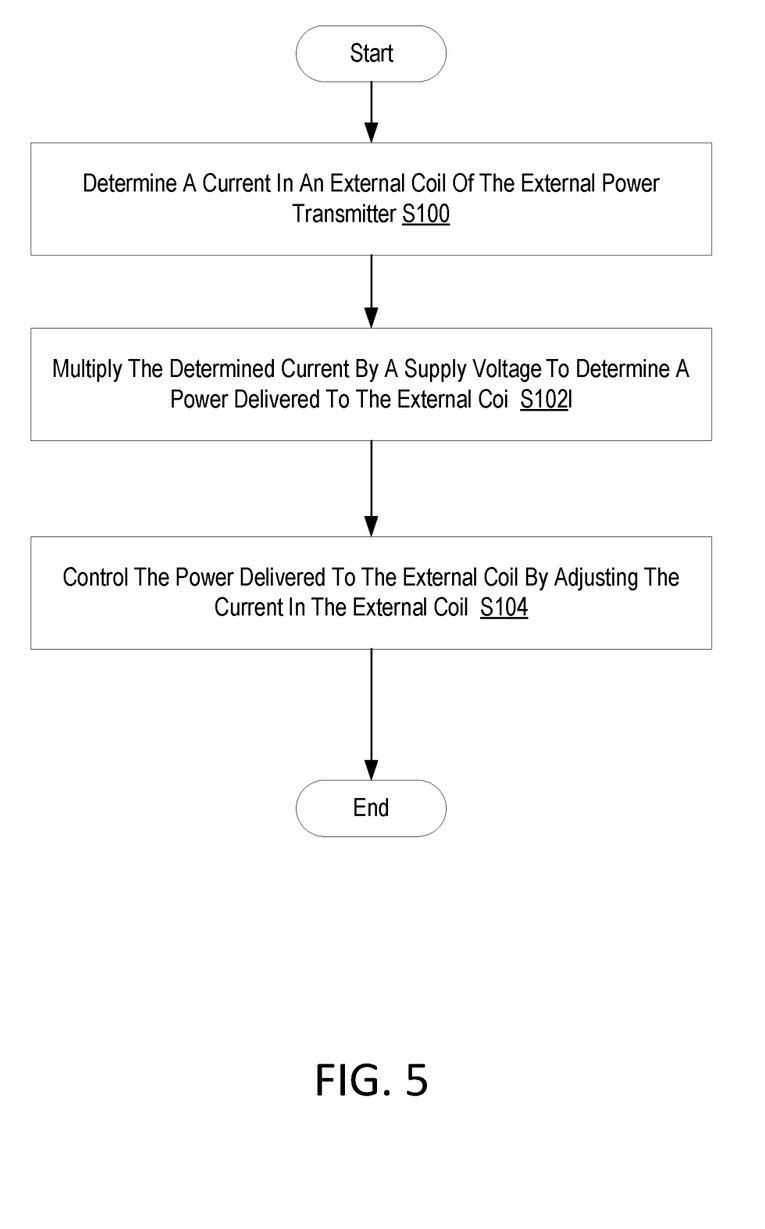
FIG. 5 is a flowchart of a process implemented in an external power transmitter of an implanted medical device according to principles set forth herein.

FIG. 5 is a flowchart of a process implemented in an external device of an implantable medical device for regulation of TETS power for an implanted medical device system. The process includes determining a current in an external coil of the external power transmitter (Block S100). The process also includes multiplying the determined current by a supply voltage to determine a power delivered to the external coil (Block S102). The process further includes controlling the power delivered to the external coil by adjusting the current in the external coil (Block S104).

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media and memory may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope of the invention, which is limited only by the following claims.

What is claimed is:

1. An external power transmitter of an implanted medical device system, the external power transmitter comprising processing circuitry configured to:
   determine a current in an external coil of the external power transmitter;
   multiply the current by a supply voltage to determine a power delivered to the external coil;
   control the power delivered to the external coil by adjusting the current in the external coil; and
   adjust the power to account for resistive losses in the external coil.

2. The external power transmitter of claim 1, wherein the processing circuitry is further configured to control the power by adjusting a duty cycle of a pulse-width-modulated bridge circuit.

3. The external power transmitter of claim 2, wherein the processing circuitry is further configured to determine the current while the pulse-width-modulated bridge circuit is active.

4. The external power transmitter of claim 3, wherein the processing circuitry is further configured to estimate the current in the external coil based at least in part on peak coil current, a pulse width of the pulse-width-modulated bridge circuit, and an approximation of the current as a sine wave.

5. The external power transmitter of claim 1, wherein the processing circuitry is further configured to use the supply voltage to compensate a current proportional integral derivative (PID) controller to maintain a constant power over different supply voltages.

6. The external power transmitter of claim 1, wherein processing circuitry is further configured to determine the current by by continuously measuring a current output of a bridge circuit.

7. The external power transmitter of claim 1, wherein the processing circuitry is further configured to determine the current by measuring a peak current in the external coil.

8. A method in an external power transmitter of an implanted medical device system, the method comprising:
   determining a current in an external coil of the external power transmitter;
   multiplying the current by a supply voltage to determine a power delivered to the external coil;
   controlling the power delivered to the external coil by adjusting the current in the external coil; and
   adjusting the power to account for resistive losses in the external coil.

9. The method of claim 8, wherein controlling the power comprises adjusting a duty cycle of a pulse-width-modulated bridge circuit.

10. The method of claim 9, wherein determining the current is performed while the pulse-width-modulated bridge circuit is active.

11. The method of claim 10, wherein determining the current in the external coil comprises estimating the current based at least in part on peak coil current, a pulse width of the pulse-width-modulated bridge circuit, and an approximation of the current as a sine wave.

12. The method of claim 8, further comprising using the supply voltage to compensate a current proportional integral derivative (PID) controller to maintain a constant power over different supply voltages.

13. The method of claim 8, wherein determining the current comprises continuously measuring a current output of a bridge circuit.

14. The method of claim 8, wherein determining the current includes measuring a peak current in the external coil.

15. A current control loop in an external device of an implanted medical device system, the current control loop including:
   an H-bridge circuit configured to output a current to an external coil of the external device;
   processing circuitry configured to:
      determine the current to the external coil based on a current output of the H bridge circuit;
      multiplying the current by a supply voltage applied to the external coil to determine a power delivered to the external coil; and
      controlling the power delivered to the external coil by adjusting the current in the external coil, the adjusting being by controlling a pulse width modulation (PWM) duty cycle of the H-bridge circuit in response to the determined current; and
   a current proportional integral derivative (PID) controller configured to control the PWM duty cycle of the H-bridge circuit.

16. The current control loop of claim 15, further comprising a current sensor configured to measure the current of the external coil, the processing circuitry being configured to compare the measured current to a current that is based on a difference between a voltage across an internal coil of the implanted medical device system and a target voltage.

17. The current control loop of claim 15, wherein the current output of the H-bridge circuit is further based on a supply voltage provided by a power supply external to the external device.

* * * * *